United States Patent
Green et al.

(10) Patent No.: US 10,131,606 B2
(45) Date of Patent: Nov. 20, 2018

(54) TETRARYLMETHANE ETHERS

(71) Applicants: Rohm and Haas Company, Philadelphia, PA (US); Dow Global Technologies LLC, Midland, MI (US)

(72) Inventors: George David Green, Cary, IL (US); Warren E. Smith, Buckinghamshire (GB); Raymond J. Swedo, Mount Prospect, IL (US)

(73) Assignees: Dow Global Technologies LLC, Midland, MI (US); Rohm and Haas Company, Midland, MI (US)

( * ) Notice: Subject to any disclaimer, the term of this patent is extended or adjusted under 35 U.S.C. 154(b) by 37 days.

(21) Appl. No.: 15/309,245

(22) PCT Filed: Apr. 21, 2015

(86) PCT No.: PCT/US2015/026820
§ 371 (c)(1),
(2) Date: Nov. 7, 2016

(87) PCT Pub. No.: WO2015/171304
PCT Pub. Date: Nov. 12, 2015

(65) Prior Publication Data
US 2017/0073290 A1     Mar. 16, 2017

Related U.S. Application Data

(60) Provisional application No. 61/990,985, filed on May 9, 2014.

(51) Int. Cl.
C07C 43/205     (2006.01)
C10L 1/00     (2006.01)

(52) U.S. Cl.
CPC .......... *C07C 43/2055* (2013.01); *C10L 1/003* (2013.01)

(58) Field of Classification Search
None
See application file for complete search history.

(56) References Cited

U.S. PATENT DOCUMENTS

| | | | |
|---|---|---|---|
| 5,981,283 | A | 11/1999 | Anderson, II et al. |
| 2014/0123549 | A1 | 5/2014 | Green et al. |
| 2014/0134746 | A1 | 5/2014 | Green et al. |
| 2015/0128485 | A1 | 5/2015 | Green et al. |

FOREIGN PATENT DOCUMENTS

| | | | |
|---|---|---|---|
| DE | 946102 | * | 7/1956 |
| JP | 06-041399 | A1 | 2/1994 |
| WO | 2014008164 | A1 | 1/2014 |
| WO | 2014165776 | A1 | 10/2014 |

OTHER PUBLICATIONS

Burton et al., Journal of the Chemical Society, 1955, 3089-92.*
Machine translation for DE 946102.*
Written translation for DE 946102, by Drapal, Jul. 16, 1956.*
Dey et al., Chemical Science (2011), 2(6), 1046-1053.*
Gong et al., Macromolecules (1997), 30(17), 4807-4813.*
CAS 154087-86-2, p. 1, 1994.*
Olsen et al. Organic & Biomolecular Chemistry (2011), 9(20), 7126-7133.*
Burton, et al., "Acylation and allied reactions catalysed by strong acids. Part XIV. Some reactions of the alpha-chlorodiphenylmethyl(+CPh2C1) and p-methoxy-triphenylmethyl cations", J. Chem. Soc., pp. 3089-3092 (1955).
Iddles, et al., "Rearrangement of the Triphenylmethyl Ether of Ortho Cresol: Direct Synthesis of 3-Methyl-4-methoxyphenyltriphenylmethane", J. Amer. Chem. Soc., vol. 62, No. 10, pp. 2757-2759 (1940).
Benkeser, et al., "Notes—Electrical Effect of the Triphenylmethyl Group on an Aromatic Ring", J. Organic. Chem., vol. 22, No. 3 (1957).
Suehiro, et al., "Aromatic triphenylmethylation reaction between benzoyl peroxides and triphenymethyl in aromatic solvents", Tetrahedron, vol. 24, No. 4 (1968).
Kirste, et al., "EPR, proton and carbon-13 ENDOR studies of a quintet state 13C-labeled galvinoxyl-type tetraradical", J. Amer. Chem. Soc., vol. 111, No. 1 (1989).
Benkeser, et al., "The Question of Orientation in the Introduction of the Triphenylmethyl Radical into Solvent Substrates of Toluene, Chlorobenzene and Methyl Benzoate. The Tritylation of Aromatic Rings Containing Deactivating Groups", J. Amer. Chem. Soc., vol. 78, No. 19, pp. 4914-4916 (1956).

* cited by examiner

Primary Examiner — Ana Z Muresan

(57) ABSTRACT

A compound having formula $C\{Ph(R^1)_i(OR^2)_j\}_2\{Ph(R^3)_m(OR^4)_n\}\{Ph(R^5)_o(OR^6)_p\}$, wherein Ph represents a benzene ring, $R^1$, $R^3$ and $R^5$ independently are $C_1$-$C_{18}$ alkyl; $R^2$, $R^4$ and $R^6$ independently are C4-C12 alkyl, i, m, n, o, and p independently are zero, one or two; j is one or two.

2 Claims, No Drawings

TETRARYLMETHANE ETHERS

This invention relates to new compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, WO2014/008164 discloses the use of trityl aryl ethers for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula $C\{Ph(R^1)_i(OR^2)_j\}_2\{Ph(R^3)_m(OR^4)_n\}\{Ph(R^5)_o(OR^6)_p\}$, wherein Ph represents a benzene ring, $R^1$, $R^3$ and $R^5$ independently are $C_1$-$C_{18}$ alkyl or $C_4$-$C_{18}$ heteroalkyl; $R^2$, $R^4$ and $R^6$ independently are $C_1$-$C_{18}$ alkyl or $C_4$-$C_{18}$ heteroalkyl, i, j, m, n, o and p independently are zero, one or two, provided that (a) at least one of i and j is not zero, or (b) at least one of m and n and at least one of o and p are not zero; that, when j is one and i, m, n, o and p are zero, then $R^2$ is not $C_9$-$C_{11}$ alkyl; and that, when n and p are one and i, j, m, and o are zero, $R^4$ and $R^6$ are not $C_9$-$C_{11}$ alkyl.

DETAILED DESCRIPTION

Percentages are weight percentages (wt %) and temperatures are in °C., unless specified otherwise. Experimental work is carried out at room temperature (20-25° C.), unless otherwise specified. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are saturated. Preferably, alkyl groups are unsubstituted. Preferably, alkyl groups are linear or branched, i.e., acyclic. Preferably, each alkyl substituent is not a mixture of different alkyl groups, i.e., it comprises at least 98% of one particular alkyl group. A "heteroalkyl" group is an alkyl group in which one or more methylene groups has been replaced by O or S. Preferably, heteroalkyl groups contain from one to six O or S atoms, preferably from one to four, preferably from one to three. The methylene groups replaced by O or S were bonded to two other carbon atoms in the corresponding alkyl group. Preferably, heteroalkyl groups do not contain S atoms. Preferably, heteroalkyl groups are saturated. Heteroalkyl groups may be substituted by OH or $C_1$-$C_{18}$ alkoxy groups, preferably OH or $C_1$-$C_6$ alkoxy groups, preferably hydroxy or $C_1$-$C_4$ alkoxy groups. Examples of heteroalkyl groups include oligomers of ethylene oxide, propylene oxide or butylene oxide having two to six units of the alkylene oxide (preferably two to four, preferably two or three) and a terminal hydroxy or $C_1$-$C_6$ alkoxy group (preferably hydroxy or $C_1$-$C_4$ alkoxy, preferably hydroxy or methoxy, preferably hydroxy); an example of an ethylene oxide oligomer is —{$(CH_2)_2O\}_xR$, where x is an integer from two to six and R is hydrogen or $C_1$-$C_6$ alkyl. Preferably, j is from two to four, preferably two or three. Preferably, R is hydrogen or $C_1$-$C_4$ alkyl, preferably hydrogen or methyl, preferably hydrogen. Preferably, the compounds of this invention contain elements in their naturally occurring isotopic proportions.

The compounds of the present invention are defined by the formula $C\{Ph(R^1)_i(OR^2)_j\}_2\{Ph(R^3)_m(OR^4)_n\}\{Ph(R^5)_o(OR^6)_p\}$ with several provisos. The first, which states that (a) at least one of i and j is not zero, or (b) at least one of m and n and at least one of o and p are not zero, excludes compounds in which the only substitution on the four benzene rings in the formula occurs on one ring. The excluded compounds would have the structure

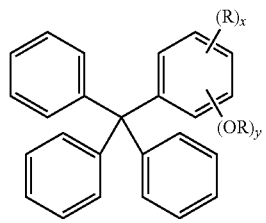

where "R" indicates any of the alkyl substituents defined herein and x and y can be zero, one or two. The compounds defined herein could not have such a structure if at least one of i and j is not zero because there are two benzene rings having substituents with this subscript, so if either i or j is not zero, there would be at least one substituent on two or more rings. This also could not occur if the other two rings both had substituents, which would occur if at least one of the substituents m and n were not zero and at least one of the substituents o and p were not zero.

The second proviso, which states that, when j is one and i, m, n, o and p are zero, then $R^2$ is not $C_9$-$C_{11}$ alkyl, excludes compounds in which the only substituents are two $C_9$-$C_{11}$ alkoxy groups, one on each of two benzene rings. The excluded compounds would have the structure

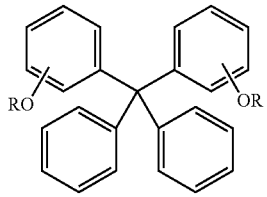

where in this case "R" indicates a $C_9$-$C_{11}$ alkyl group. The third proviso, which states that, when n and p are one and i, j, m, and o are zero, $R^4$ and $R^6$ are not $C_9$-$C_{11}$ alkyl, also excludes these compounds. Preferably, the second and third provisos exclude $C_8$-$C_{12}$ alkyl groups.

Preferably, at least one of $R^1$, $R^2$, $R^3$, $R^4$, $R^5$ and $R^6$ has at least three carbon atoms, preferably at least four carbon atoms, preferably at least five. Preferably, all of the "R" groups on the compound collectively have at least six carbon atoms, preferably at least eight, preferably at least ten, preferably at least twelve; preferably no more than thirty-five, preferably no more than thirty, preferably no more than twenty-five. In one preferred embodiment, j is one or two, preferably two. Preferably, $R^1$, $R^3$ and $R^5$ independently are $C_1$-$C_{16}$ alkyl or $C_4$-$C_{16}$ heteroalkyl, preferably $C_1$-$C_{16}$ alkyl, preferably $C_1$-$C_{12}$ alkyl, preferably $C_3$-$C_{12}$ alkyl, preferably $C_3$-$C_8$ alkyl, preferably $C_4$-$C_{12}$ alkyl. Preferably, $R^1$, $R^3$ and $R^5$ are saturated. Preferably, $R^1$, $R^3$ and $R^5$ are linear or branched. Preferably, $R^2$, $R^4$ and $R^6$ independently are $C_1$-$C_{16}$ alkyl or $C_4$-$C_{16}$ heteroalkyl, preferably $C_1$-$C_{16}$ alkyl, preferably $C_1$-$C_{12}$ alkyl, preferably $C_3$-$C_{12}$ alkyl, preferably $C_3$-$C_8$ alkyl, preferably $C_4$-$C_{12}$ alkyl. Preferably, $R^2$, $R^4$ and $R^6$ are saturated. Preferably, $R^2$, $R^4$ and $R^6$ are linear or branched.

The compounds of this invention can be depicted as follows:

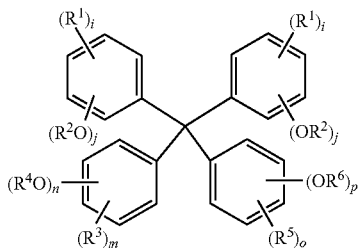

In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectable by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art, e.g., allowing a substituted benzene (substituted with alkyl and/or hydroxyl groups) to react with a carbon tetrahalide and a Lewis acid to form a substituted dihalobenzophenone precursor, then allowing said precursor to react with another substituted benzene to form a substituted tetraphenylmethane. Hydroxyl groups on the substituted tetraphenylmethane can be converted to alkyl ethers by reaction with, e.g., an alkyl halide, in the presence of a base, e.g., alkali metal hydroxides, preferably in a polar aprotic solvent, e.g., DMSO, NMP, DMAc. Another method comprises allowing a substituted benzophenone, which may be asymmetric, to react with a halogenating agent, e.g., phosphorus pentachloride, to form a substituted dichlorodiphenylmethane, followed by reaction with a substituted or unsubstituted phenol under Friedel-Crafts conditions.

Examples

Syntheses of 4,4'-Dihydroxytetraphenylmethane (DHTPM) Ethers

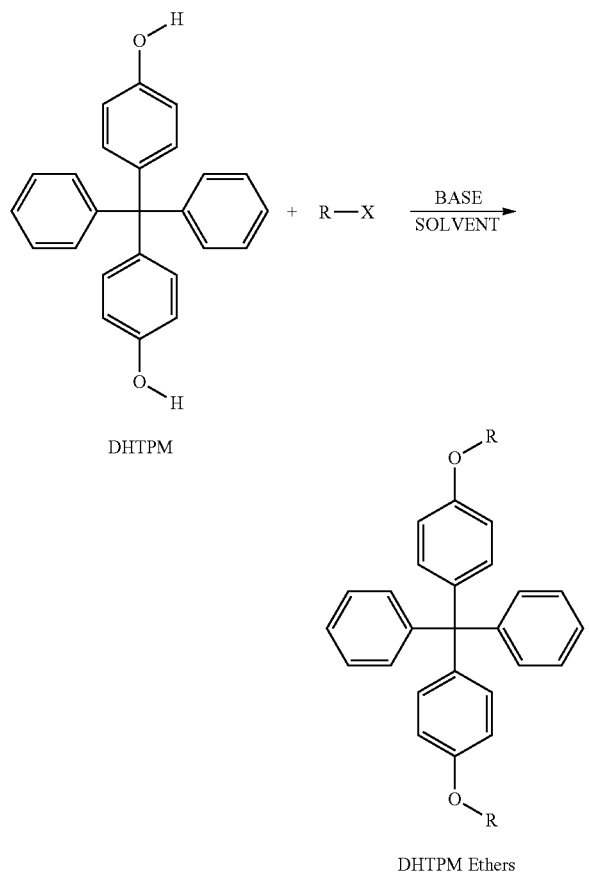

X = Cl, Br

1) Bis(4-(pentyloxy)phenyl)diphenylmethane (BPentTPM)

A 125 mL 3-neck flask was equipped with a magnetic stirrer, a reflux condenser with nitrogen blanket, and a heating mantle with a temperature controller and a thermocouple. The flask was charged with 3.54 grams (0.01 moles) of 4,4'-dihydroxy-tetraphenylmethane (DHTPM), 1.35 grams (0.02 moles) of potassium hydroxide (KOH) pellets, and 40 mL of dimethylsulfoxide (DMSO). The mixture was stirred under nitrogen and was heated to 100° C. The KOH was completely dissolved by the time the temperature reached 100° C. The reaction mixture was cooled to below 50° C., and then 2.48 mL (d 1.218; 3.02 grams; 0.02 moles) of 1-bromopentane were added in one portion. An exotherm of about 8° C. was noted. The reaction mixture was then heated to 70-75° C., the reaction being monitored by GPC analyses. Solids began to separate out from the mixture as soon as the reaction mixture temperature reached about 60° C. After 3 hours at 70-75° C., the reaction mixture was poured into about 250 mL of water containing about 25 grams of sodium chloride and a few pellets of KOH. Toluene (about 150 mL was added, and the mixture was stirred at room temperature for about 30 minutes. The mixture was transferred to a separatory funnel, and the layers were separated. The lower, aqueous, layer was extracted with 1×50 mL of toluene. The toluene layers were combined and were washed with 1×50 mL of saturated aqueous sodium chloride solution, and were then dried over anhydrous magnesium sulfate. The toluene mixture was filtered, and the solvent was removed by rotary evaporation to give 4.35 grams (88.2% yield) of BPentTPM as a light brown crystalline solid. MP=110-113° C. The structure of the product was confirmed by IR, NMR, and GC/MS analyses.

2) Bis(4-hexyloxy)phenyl)diphenylmethane (BHexTPM)

This ether was synthesized as described above from 3.52 grams (0.01 moles) of DHTPM, 1.34 grams (0.02 moles) of KOH, 25 mL of DMSO, and 2.81 mL (d 1.176; 3.30 grams; 0.02 moles) of 1-bromohexane. The reaction mixture was heated at 70-75° C. for 3 hours after the addition of the bromide. The yield of product as a beige solid was 4.64 grams (89.1%). MP=120-122° C. The structure of the product was confirmed by IR, NMR, and GC/MS analyses.

3) Bis(4-(heptyloxy)phenyl)diphenylmethane (BHeptTPM)

This ether was synthesized as described above from 3.53 grams (0.01 moles) of DHTPM, 1.34 grams (0.02 moles) of KOH, 40 mL of DMSO, and 3.14 mL (d 1.14; 3.58 grams; 0.02 moles) of 1-bromoheptane. The reaction mixture was heated at 70-75° C. for 5.5 hours after the addition of the bromide. The yield of product as a beige crystalline solid was 5.06 grams (92.2%). MP=103-105° C. The structure of the product was confirmed by IR, NMR, and GC/MS analyses.

4) Bis(4-(octyloxy)phenyl)diphenylmethane (BOctTPM)

This ether was synthesized as described above from 3.53 grams (0.01 moles) of DHTPM, 1.4 grams (0.029 moles) of KOH, 40 mL of DMSO, and 3.45 mL (d 1.118; 3.86 grams; 0.02 moles) of 1-bromooctane. The reaction mixture was heated at 70-75° C. for 8 hours after the addition of the bromide. GPC analyses showed the presence of some remaining DHTPM. Upon work up, the amount of KOH present in the aqueous solution was increased from a few pellets to about 5 grams, and the mixture was stirred at room temperature overnight instead of for only 30 minutes. The yield of product as a beige crystalline solid was 5.29 grams (91.7%). MP=84.5-86.5° C. The structure of the product was confirmed by IR, NMR, and GC/MS analyses.

Analyses

1. IR Analyses:

IR analyses were performed using a Nicolet 560 FTIR spectrometer. For liquid samples, a small drop was cast as a neat film between two KBr plates. For solid samples, KBr dispersions were pressed. The IR spectrum was acquired in the transmission mode from 4000 to 400 cm$^{-1}$, with a spectral resolution of 4 cm$^{-1}$. A Happ-Genzel type apodization function was used.

2. NMR Analyses:

Both $^1$H and $^{13}$C NMR spectra were acquired using a Bruker 200 NMR spectrometer operating at 4.7 T. $^1$H spectra were obtained using an 8.2 second accumulation time and 2.0 KHz sweep width; the $^{13}$C spectra were obtained at a 4.7 second accumulation time and 7.0 KHz sweep width. Methanol-d$_4$ was typically used as the solvent. Chemical shifts were referenced using the solvent resonances at 3.30 ppm for $^1$H, and at 59.05 ppm for $^{13}$C.

3. GPC Analyses:

GPC analyses to follow the progress of synthesis reactions and to determine product purity were performed using a PerkinElmer Series 200 HPLC. Two Polymer Laboratories pLgel columns were used in series: 1) 300 mm×7.5 mm, 3μ, 100 Å and 2) 300 mm×7.5 mm, 5μ, 50 Å. These two columns were preceded by a guard column. The columns were maintained at 35° C. The mobile phase was 100% THF at a flow rate of 2 mL/minute. UV detection was at 270 nm. The program run time was 10 minutes.

4. GC/MS Analyses:

These analyses gave GC retention time and MS fragmentation data, and were performed using a Hewlett Packard Model 6890 GC system with an Agilent Mass Selective Detector operating in electron ionization (EI) mode and in positive chemical ionization (CI) mode. The carrier gas for the EI mode was helium at approximately 1 mL/minute. Methane was used as the carrier gas for the CI mode. The column was a J&W Scientific DB-5MS, 30 meter×0.25 mm×1 μm film. The initial oven temperature was 60° C. with a hold time of 5 minutes. The temperature was ramped at 10° C./minute to 220° C. with a hold of 2 minutes, and then it was ramped at 20° C./minute to 290° C. The injector temperature was 225° C. The sample size was 1 μL for EI mode, and 1 μL for CI mode. The split ratio was 50:1.

5. Melting Points:

Melting points were determined using a Mel-Temp apparatus, and are uncorrected.

Detection and Linearity Study for BHexTPM

Instrument: 6890 GC with 5973 MSD, and 7683B autosampler

Injection port: 280° C., 3 μL injection, splitless

Column: DB-35, 15 m, 0.255 mm ID, 0.25 μm film

Flow: 1.4 mL/min He

Oven: 100° C., hold 0 min, ramp 20° C./min to 280° C., hold 10 min, ramp 20° C./min to 340° C., hold 5 min Aux transfer line: 280° C.

Solvent delay: 17 min

Mass detection mode: SIM mode, for ions 343.3, 443.4, 520.4 (0.7-0.9 amu)

Dwell time: 100 msec

MS Source: EI, 250° C.

MS Quad: 200° C.

Sample Dilution:

Stock 1: 10 mg BHexTPM dissolved in 25 mL xylene

Stock 2: 0.5 mL Stock 1 diluted to 25 mL in xylene 1000 ppb: 1.25 mL Stock 2 diluted to 10 mL in Turkish diesel 500 ppb: 625 μL Stock 2 diluted to 10 mL in Turkish diesel 250 ppb: 312.5 μL Stock 2 diluted to 10 mL in Turkish diesel 100 ppb: 1 mL of 1000 ppb stock diluted to 10 mL in Turkish diesel 50 ppb: 1 mL of 500 ppb stock diluted to 10 mL in Turkish diesel

| ppb | Ret Time | Width | Area | Start Time | End Time |
|---|---|---|---|---|---|
| 1000 | 23.000 | 0.066 | 9887889 | 22.911 | 23.192 |
| 500 | 23.000 | 0.071 | 5125725 | 22.907 | 23.298 |
| 250 | 23.001 | 0.072 | 2493155 | 22.907 | 23.274 |
| 100 | 23.000 | 0.074 | 1039475 | 22.854 | 23.298 |
| 50 | 22.998 | 0.07 | 507502 | 22.854 | 23.274 |

Results of linear regression analysis: Area=9888.8×concentration+53010; $R^2$=0.9996

| STRUCTURE | MP, ° C. | GC RET. TIME (min) | MS Masses | Solubility @ 10% @ −10 C. | GPC RET TIME (MIN) |
|---|---|---|---|---|---|
| BPentTPM FW 492.69 | 110-113 | 21.9 | 492, 415, 329 | | 6.8 |
| BHexTPM FW 520.74 | 120-122 | 23.1 | 520, 443, 343 | | 6.68 |

-continued

| STRUCTURE | MP, °C. | GC RET. TIME (min) | MS Masses | Solubility @ 10% @ −10 C. | GPC RET TIME (MIN) |
|---|---|---|---|---|---|
| 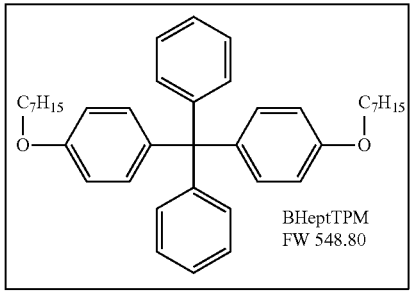 BHeptTPM FW 548.80 | 103-105 | 24.4 | 548, 471, 357 | | 6.61 |
| 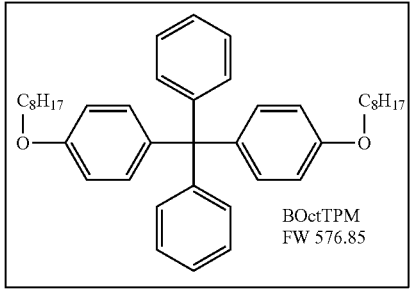 BOctTPM FW 576.85 | 84.5-86.5 | 26.2 | 576, 499, 371 | | 6.57 |

The invention claimed is:

1. A compound of formula $C\{Ph(R^1)_i(OR^2)_j\}_2\{Ph(R^3)_m(OR^4)_n\}\{Ph(R^5)_o(OR^6)_p\}$, wherein Ph represents a benzene ring, $R^1$, $R^3$ and $R^5$ independently are $C_1$-$C_{18}$ alkyl; $R^2$, $R^4$ and $R^6$ independently are $C_4$-$C_{12}$ alkyl, i, m, n, o and p independently are zero, one or two; j is one or two; and all $R^1$, $R^2$, $R^3$, $R^4$, $R^5$ and $R^6$ substituents collectively have a total of eight to thirty-five carbon atoms, wherein alkyl groups are saturated and unsubstituted, provided that when j is one and i, m, n, o and p are zero, then $R^2$ is not $C_9$-$C_{11}$ alkyl.

2. The compound of claim 1 in which $R^1$, $R^2$, $R^3$, $R^4$, $R^5$ and $R^6$ are acyclic.

* * * * *